United States Patent

Sugimoto et al.

Patent Number: 5,877,498
Date of Patent: Mar. 2, 1999

[54] METHOD AND APPARATUS FOR X-RAY ANALYSES

[75] Inventors: Aritoshi Sugimoto, Tokyo; Yoshimi Sudo, Hachioji; Tokuo Kure, Tokyo; Ken Ninomiya, Higasgi-Matsuyama; Katsuhiro Kuroda, Hachioji; Takashi Nishida, Tokyo; Hideo Todokoro, Tokyo; Yasuhiro Mitsui, Fuchu; Hiroyasu Shichi, Tanashi, all of Japan

[73] Assignee: Hitachi, Ltd., Tokyo, Japan

[21] Appl. No.: 893,034

[22] Filed: Jul. 15, 1997

Related U.S. Application Data

[63] Continuation-in-part of Ser. No. 782,929, Jan. 13, 1997, abandoned, which is a continuation of Ser. No. 430,535, Apr. 25, 1995, Pat. No. 5,594,246, which is a continuation-in-part of Ser. No. 211,575, filed as PCT/JP93/01373 Sep. 27, 1993, Pat. No. 5,481,109.

[30] Foreign Application Priority Data

Sep. 28, 1992 [JP] Japan ................................. 4-257789
Apr. 28, 1994 [JP] Japan ................................. 6-091034

[51] Int. Cl.⁶ .......................... G01N 23/225; H01J 37/256
[52] U.S. Cl. .......................................... 250/310; 250/307
[58] Field of Search ..................................... 250/310, 307

[56] References Cited

U.S. PATENT DOCUMENTS

| | | | |
|---|---|---|---|
| 4,570,072 | 2/1986 | Kimura et al. | 250/397 |
| 4,697,080 | 9/1987 | King | 250/310 |
| 5,481,109 | 1/1996 | Ninomiya et al. | 250/310 |
| 5,594,246 | 1/1997 | Sudo et al. | 250/310 |

FOREIGN PATENT DOCUMENTS

| | | |
|---|---|---|
| 55-3129 | 1/1980 | Japan . |
| 61-132847 | 6/1986 | Japan . |
| 63-243855 | 10/1988 | Japan . |
| 5-52779 | 3/1993 | Japan . |
| 5-190633 | 7/1993 | Japan . |

OTHER PUBLICATIONS

Optical Systems For Soft X–Rays, Alan Michette, pp. 17–23.

*Primary Examiner*—Jack I. Berman
*Attorney, Agent, or Firm*—Fay, Sharpe, Beall, Fagan, Minnich & McKee

[57] ABSTRACT

An X-ray analyzing method for inspecting opening states of fine holes comprises the steps of: irradiating a finely converged electron beam into a first fine hole, observing an X-ray emitted from the inside of said first fine hole in order to obtain an first X-ray analysis data about the residue substance existing at the bottom of said first fine hole; irradiating a finely converged electron beam into a second fine hole, observing an X-ray emitted from the inside of said second fine hole in order to obtain an second X-ray analysis data about the residue substance existing at the bottom of said second fine hole; and comparing said first X-ray analysis data with said second X-ray analysis data, forming a judgment as to whether or not a difference between said first and second analysis data is smaller than a predetermined threshold value and using an outcome of said judgment to determine the opening states of said first and second fine holes. The X-ray observations are carried out by detecting only the X-rays emitted within the angular range $-\theta$ to $+\theta$ where notation $\theta$ is an angle formed with a center axis of the irradiated electron beam and so defined that $\tan \theta$ is equal to a/d whereas notations a and d are the radius and the depth of the fine holes.

20 Claims, 12 Drawing Sheets

$\tan \theta = a/d$

METHOD AND APPARATUS FOR X-RAY ANALYSES

CROSS-REFERENCE TO RELATED APPLICATION

The present invention is a continuation-in-part application of a copending application Ser. No. 08/782,929 now abandoned filed on Jan. 13, 1997; which is incorporated by reference herein in its entirety. The copending application Ser. No. 08/782,929 is a continuation application of a prior application Ser. No. 08/430,535 filed on Apr. 25, 1995, which is now patented as U.S. Pat. No. 5,594,246 issued Jan. 14, 1997. And, the prior application Ser. No. 08/430,535 is a continuation-in-part application of a former application Ser. No. 08/211,575, filed as PCT/JP93/01373 Sep. 27, 1993, which is now patented as U.S. Pat. No. 5,481,109 issued Jan. 2, 1996.

BACKGROUND OF THE INVENTION

The present invention relates to a surface-analysis technique in general and to an X-ray analysis method and apparatus of residue on the surface of a specimen or a sample in particular.

In order to promote the large-scale integration of semiconductor devices, it is necessary to establish a fine-line patterning process technology at a level smaller than the deep submicron. In the manufacturing of 1-Gb DRAMs (Dynamic Random-Access Memories), for example, a patterning process of a contact hole having a diameter of 0.16 $\mu$m and a depth of 2 $\mu$m is required. In order to establish such a fine-line patterning process, technologies of analysis for measuring and inspecting the accuracy of the fine-line patterning are necessary. In particular, technologies of analysis that can be used for analyzing the composition and thickness of residue are required. In this residue analysis, points to be taken into consideration are the fact that the surface of the sample (wafer) is not necessarily flat so that areas having large steps such as a small contact hole described earlier also need to be analyzed as well.

The conventional residue analysis for analyzing areas having large steps is carried out by destructing a fabricated wafer and observing the cross section of the destructed wafer by means of an SEM (Scanning Electron Microscope). With this technique, however, the composition of the residue cannot be identified only by observation of the shape and, on top of that, the wafer cannot be returned to the manufacturing process after the analysis once the wafer has been destructed. Other problems with this technique include the fact that it is difficult to observe a trace of residue of the order of few nm. In the development of semiconductor integrated-circuit devices after Gb, the above problems which entail deterioration of the yield and the precision of analysis are regarded as fatal problems.

On the other hand, an X-ray analysis method, which is an analysis technique allowing analyses to be done without destructing a wafer, is available. An example of a typical X-ray analysis method is the use of charged-particle analysis equipment disclosed in Japanese Patent Laid-open No. Sho 63-243855. With this charged-particle analysis equipment, an irradiated electron beam is applied to the surface of a sample. An X-ray generated from the surface of the sample due to the application of the irradiated electron beam thereto is then observed. The X ray is observed by means of a light splitting crystal placed at an angle of about 22 degrees from the center axis of the electron beam.

In order to carry out qualitative and quantitative analyses on residue by using X-rays, the place at which a means for observing the X-rays is installed is important. Specifically, in order to prevent the X-rays generated by the surface of the sample from being absorbed by an obstacle, the means for observing the X-ray must be placed at a location where no such obstacle exists. Unfortunately, however, there has been so far no clear standard concerning the location for installing a means for observing the X-rays and no much attention has hence been paid to such an installation position. In the case of the charged-particle analysis equipment mentioned above, a light splitting crystal is positioned at an angle of 22 degrees. None the less, the absorption of the X-rays cannot be avoided in some cases. In particular, in the case of large-scale integrated memories beyond the 4-Mb DRAM which are considered to be the main semiconductor devices in the future, by merely using the charged-particle analysis equipment, it will be impossible to perform qualitative and quantitative analyses of residue on the surface of a sample.

SUMMARY OF THE INVENTION

It is an object of the present invention to provide an X-ray analysis method and apparatus which can be used for carrying out qualitative and quantitative analyses of residue on the surface of a sample with a high degree of sensitivity without destructing the sample.

In order to achieve the object, the present invention provides an electron-beam irradiating means for irradiating and focusing a low accelerated electron beam and applying the electron beam to the surface of a sample, and an X-ray observing means for observing an X-ray generated by the surface of the sample due to the application of the irradiate electron beam thereto from a position in a direction close to the irradiated electron beam.

When an irradiated electron beam is applied to a substance, X-rays are generated by the substance. The energy (or wavelength) of the generated X-rays is an inherent quantity of the element making up the substance. Accordingly, the element and, hence, the substance can be identified by analyzing the energy of the generated X-rays. Such an analysis is known as a qualitative analysis. In addition, information on the quantity of the substance (or the film thickness) can be obtained from the intensity of the irradiated X-rays. An analysis that results in information on the film thickness is called a quantitative analysis.

In order to allow an analysis to be performed on residue even on areas having large steps without destructing the sample (or wafer), a method of observing an X-ray generated from the surface of the sample is important. There are two types of main residue in a process of manufacturing semiconductor devices: a silicon oxide film and a photoresist layer. In order to identify components of these residues, X-rays generated by light elements such as the C (carbon), o (oxygen) and Si (silicon) atoms must be detected. The amount of energy of a CK$\alpha$ X-ray or an OK$\alpha$ X-ray generated by the application of an irradiated electron beam to a substance has a small value of less than 1 keV. Accordingly, such an X-ray cannot pass through an obstacle which may exist, if any, between a location generating the X-ray and a means for observing the X-ray. As a result, the X-ray cannot be observed. Although the X-rays pass through an obstacle, most X-rays are so absorbed by the obstacle as to be unable to be detected. The state of X-ray observation is described in more detail below by citing an example of an analysis of residue inside a fine hole which must be carried out under most severe observation conditions. An example of a fine hole is the contact hole mentioned earlier.

FIG. 2 shows an incident electron beam 1 entering a fine hole H on the surface of a sample 2. As described previously, a generated X-ray 5 must be observed from a position in a direction where no obstacle exists between the location generating the X-ray and the observation means. Namely, it is necessary to observe the X-rays 5 from a position in an area A in FIG. 2 covering what is referred to hereafter as directions close to the electron beam. Here, an angle θ is so defined that tan θ is equal to a/d where notations a and d are the radius and the depth of the fine hole H respectively. In the case that the X-rays which passed through an obstacle are strong enough to be detected, the angle θ becomes slightly larger than arctan (a/d). The attenuations of the X-rays during passing through an obstacle depend not only on the energy of the X-rays and the elements included in the obstacle, but dominantly on the transmission distance of the X-rays inside the obstacle. That is, the angle θ may be defined that tan θ is substantially equal to a/d. When thinking of large-scale integration of future semiconductor devices such as memory products beyond the 4-Mb DRAM, it is necessary to observe X-rays generated by a contact hole from a position on a direction that forms, with the electron beam, a θ angle of smaller than 20 degrees. In the charged-particle analysis equipment disclosed in Japanese Patent Laid-open No. Sho 63-243855 cited previously, a light splitting crystal for observing generated X-rays is located at a position in a direction forming a θ angle of 22 degrees with the center axis of the electron beam. Accordingly, the charged-particle analysis equipment cannot be applied to the analysis of residue in a contact hole of a device beyond the 4-Mb DRAM. In contrast to this equipment, a means provided by the present invention for observing X-rays is designed by consideration to include an X-ray detector, a detecting surface of which is partially or completely located in an area with a θ angle cited above of smaller than 20 degrees or the area A shown in FIG. 2, or to include an optical device partially or totally located in the area A for leading the X rays to the X-ray detector. A variety of techniques can be thought of as a means for observing an X-ray. These techniques are explained one after another through the following detailed description of preferred embodiments.

As described above, by applying an irradiated electron beam to the surface of a sample and observing X-rays generated by the surface from a position in a direction close to the electron beam, qualitative and quantitative analyses can be carried out on residue on the surface of a sample with large steps such as contact holes, to say nothing of a sample with small steps.

These and other objects and many of the attendant advantages of the present invention will be readily appreciated as the same becomes better understood by reference to the following detailed description when considered in connection with accompanying drawings.

DETAILED DESCRIPTION OF THE PREFERRED EMBODIMENTS

The present invention will become apparent from the following detailed description of preferred embodiments with reference to accompanying diagrams.
Embodiment 1

Figure 1:
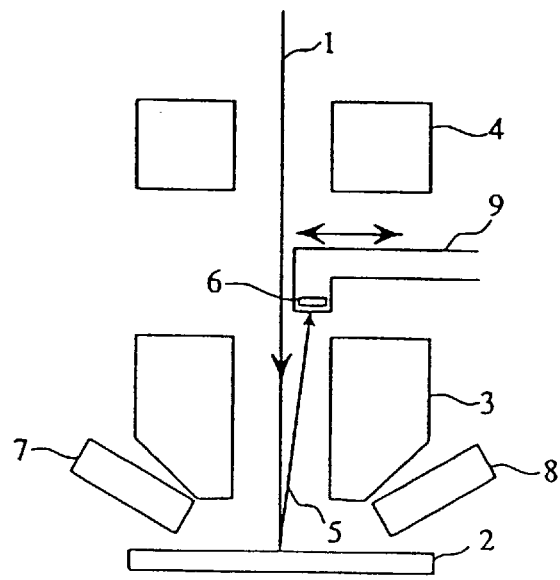
FIG. 1 is a cross-sectional model diagram showing a simplified configuration of an embodiment implementing an X-ray analysis apparatus in accordance with the present invention.

A most basic embodiment provided by the present invention is shown in FIG. 1. As shown in the figure, an accelerated electron beam 1 is applied perpendicularly to the surface of a sample 2. Here, the electron beam 1 is converged so that the diameter of the beam is decreased to a sufficiently small value in comparison with the size of a deposition region of residue on the surface of the sample 2 to be analyzed. An example of the size of such a deposition region is the diameter of a fine hole. In this way, the accelerating energy of the electron beam 1 is controlled to a value smaller than 5 keV. The electron beam 1 is converged by means of an objective lens 3 and a condenser lens 4.

The application of the irradiated electron beam 1 to the surface of the sample 2 causes an X-ray 5 to be generated by the residue on the surface of the sample 2. The X-ray 5 is detected by a detector 6 installed at a position in a direction close to the electron beam 1 between the objective lens 3 and the condenser lens 4. Having an energy analyzing function, a representative detector 6 includes an X-ray solid-state detector and a parpicon (imaging tube). A significant point to be taken into consideration in the installation of the detector 6 is that the detector 6 must be installed so that a surface thereof for detecting the X-ray 5 is partially or completely located inside the area A shown in FIG. 2. In order to install the detector 6 in this way, it is thus necessary to place the detector 6 at a position as close as possible to the electron beam 1 so as to make the gap between the detector 6 and the electron beam 1 have a value of the order of 1 mm. Therefore, it is essential to converge the electron beam 1 into a sufficiently thin beam so that it does not hit the detector 6. By measuring the energy and the intensity of the X-ray 5 by means of the detector 6, a qualitative and quantitative analysis of the residue can be carried out.

An X-ray having much energy such as the SiKα X-ray can penetrate a substance with a thickness of the order of several $\mu$m. Such a high-energy X-ray can be detected even by a detector 7 installed beside the unit that irradiates the electron beam. Again, this detector 7 can be an X-ray solid-state detector or the like which has an energy analyzing function. By comparing signal intensities detected by the detectors 6 and 7, the attenuation factor of an X-ray passing through a substance can be obtained. From the attenuation factor, the thickness of the substance can, in turn, be derived. By using this information, it is possible to find, for example, the depth of a fine hole on the surface of the sample 2.

The application of the electron beam 1 to the surface of the sample 2 also causes secondary electrons to be generated therefrom as well. A secondary-electron detector 8 is provided for detecting the secondary electrons. By detecting secondary electrons while scanning the electron beam 1 over the surface of the sample 2, a secondary-electron image can be obtained. By making use of the secondary-electron image, information on the position of residue can be obtained with ease and the position can also be set easily.

The detector 6 is installed in a housing 9 which can be moved in a direction denoted by an arrow in the figure. This scheme allows the distance from the housing 9 to the electron beam 1 to be kept constant all the time even in the case of an X-ray analysis conducted by varying the accelerating voltage and converging conditions of the electron beam 1.

In a qualitative and quantitative analysis of a residual substance existing on the bottom surface of a fine hole such as a contact hole through detection of an X-ray generated by application of an irradiated electron beam to the residual substance, an X-ray observing means must be installed at a position above the fine hole close to the center axis of the irradiated electron beam so that an area on the bottom surface of the fine hole generating the X-ray can be viewed directly from the position in order to avoid absorption of the generated X ray by the sidewall of the fine hole. When taking the X-ray observing means to a position close to the center axis of the electron beam, it is necessary to exercise caution so as to prevent the X-ray observing means from having a bad effect on the irradiated electron beam. For this reason, it is desirable to make up components, which constitute the X-ray detector 6, from a non-magnetic material such as aluminum, copper or stainless steel completing demagnetization treatment. In addition, in the case of an X-ray detector 6 enclosed in a housing 9 as described earlier, it is likewise desirable to make up at least components on the side of the X-ray detector 6 facing the electron beam 1 including the housing 9 from the non-magnetic material described above.

Figure 2:
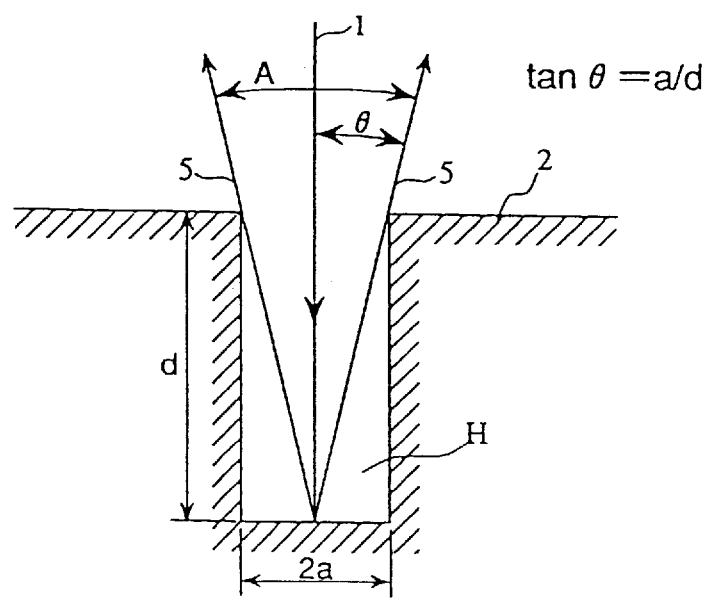
FIG. 2 is a cross-sectional model diagram used for explaining a position at which an X-ray detector is installed.
Figure 12:
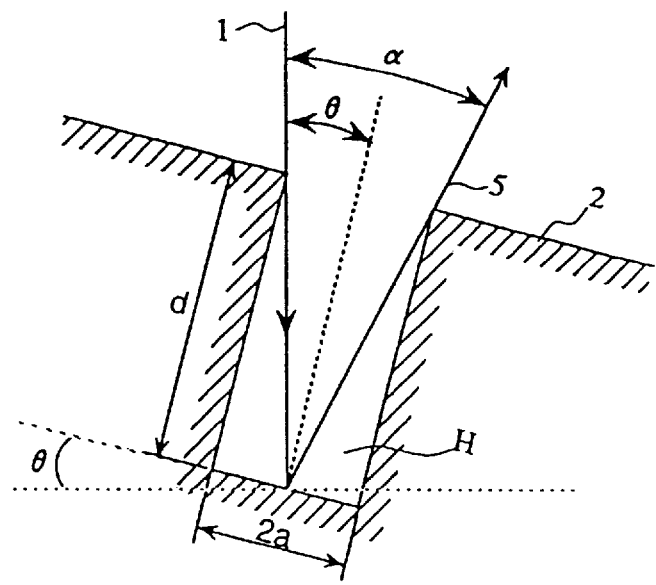
FIG. 12 is a cross-sectional model diagram used for explaining a position at which an X-ray detector is installed in the case of a slanting sample.

FIGS. 1 and 2 show configurations in which the electron beam 1 is applied perpendicularly to the bottom surface of the sample 2. By slanting the sample 2, the permissible range of angles, at which the X-ray generated from the bottom surface of the fine hole is detected, can be increased. Let, for example, the sample 2 be slanted from the horizontal direction by an angle θ as shown in FIG. 12. It should be noted that θ has previously been so defined that tan θ is equal to a/d where notations a and d are the radius and the depth of the fine hole respectively. In this case, an angle α at which the X-ray can be observed from a position above the fine hole without being obstructed by the sidewall of the fine hole is equal to 2×θ, resulting in a permissible range of angles of detection twice as much that with the sample 2 not slanting. In this way, by slanting the surface of the sample 2 relatively to the irradiated electron beam 1, the permissible range of angles for detecting the X-ray can be widened, allowing the sensitivity the X-ray detection to be increased by that much. On top of that, the X-ray can be observed with ease.

Figure 13:
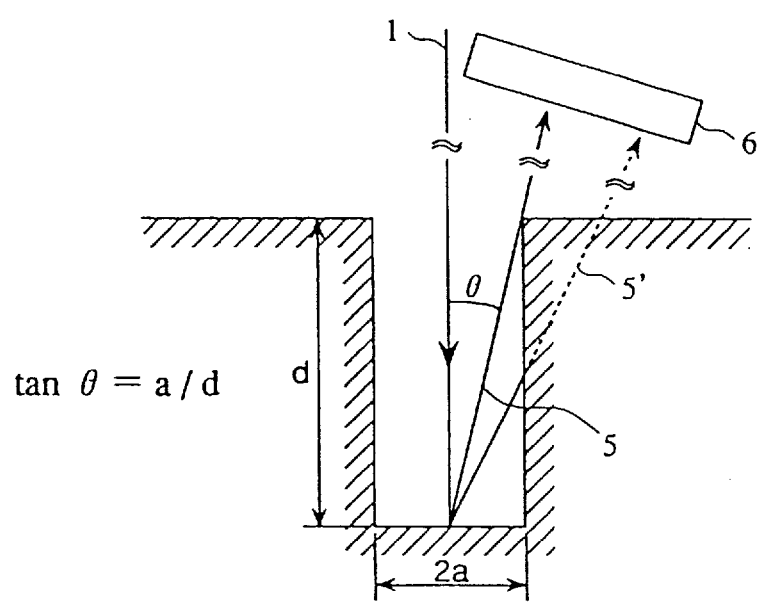
FIG. 13 is a cross-sectional model diagram used for explaining the state of an X-ray arriving at a detector after passing through a sample.
Figure 14:
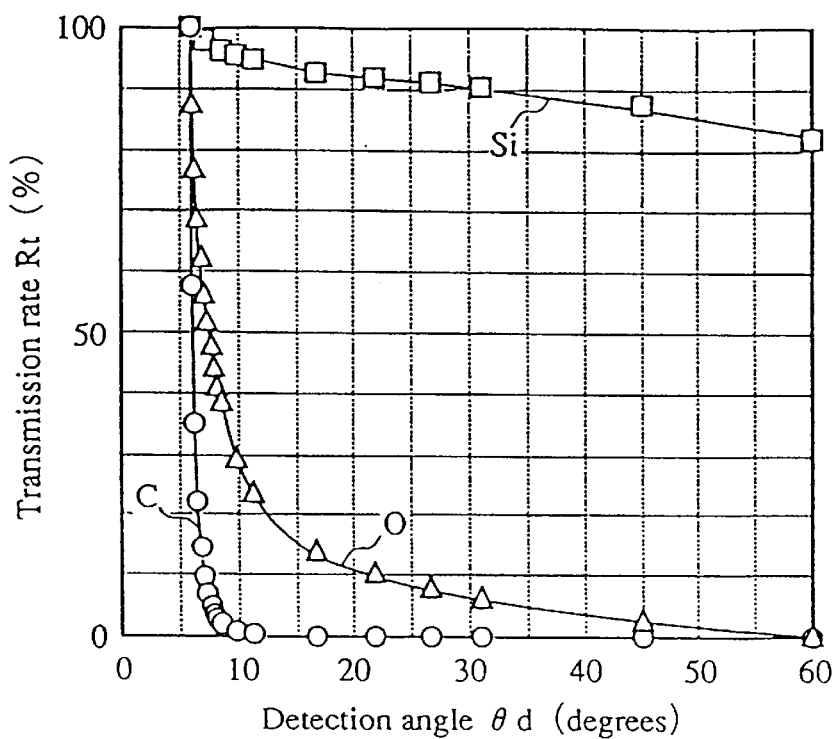
FIGS. 14 and 15 are diagrams showing curves representing relations between the angle of detection of the X-ray shown in FIG. 13 and the transmission rate.

It should be noted that the permissible range of angles formed with the center axis of the electron beam at which the X-ray is observed is not necessarily limited to the ranges of angles θ and α shown in FIGS. 2 and 12 respectively. As shown in FIG. 13, X-rays generated from the bottom surface of the fine hole by the application of an irradiated electron beam thereto also include an X-ray 5' penetrating the sidewall of the fine hole before arriving at the detector 6 in addition to an X-ray 5 which arrives at the detector 6 without being obstructed by the sidewall of the fine hole. In this case, the transmission rate of the penetrating X-ray 5' has a variable value depending upon the material which the sidewall of the fine hole is made of, the type (or the energy) of the X-ray or the hole size (that is, the diameter and depth) of the fine hole. Let, for example, the material of the sidewall be a resist film as is the case with a contact hole of a semiconductor device. In this case, dependence of the transmission rate $R_t$ of the X-ray generated from an element such as C (carbon), O (oxygen) or Si (silicon) cited earlier on the angle of detection ($\theta_d$) formed with the center axis of the irradiated electron beam is shown in FIG. 14. By the transmission rate $R_t$, a rate at which an X-ray penetrates the resist-film sidewall, arriving at the detector 6 is meant. It should be noted that the figure shows dependence for the following hole dimensions: a hole diameter (2a) of 0.2 $\mu$m, a depth (d) of 1 micrometer and an aspect ratio d/2a of 5.0. In this case, the angle θ is previously so defined that tan θ is equal to a/d which is 5.71 degrees. It is obvious from the figure that a carbon X-ray is almost entirely absorbed as soon as it enters the resist film. For an angle of detection $\theta_d$ exceeding the angle θ (=5.71 degrees), the carbon X-ray cannot thus be observed. As a result, the angle of detection $\theta_d$ must be smaller than the angle θ in order for the carbon X-ray to be able to arrive at the detector 6. On the other hand, an oxygen X ray passes through the resist film at a transmission rate of about 10% and is hence able to arrive at the detector 6 even if the angle of detection is set at 20 degrees. As for a silicon X-ray, the rate of absorption by the resist film is very low. Accordingly, the silicon X ray passes through the resist film at a transmission rate of about 80% and is therefore able to arrive at the detector 6 even if the angle of detection is set at 60 degrees. For this reason, an X-ray having energy higher than those of silicon and aluminum can also be observed at an angle of greater than 22 degrees from the center axis of the electron beam as is generally known.

Figure 15:
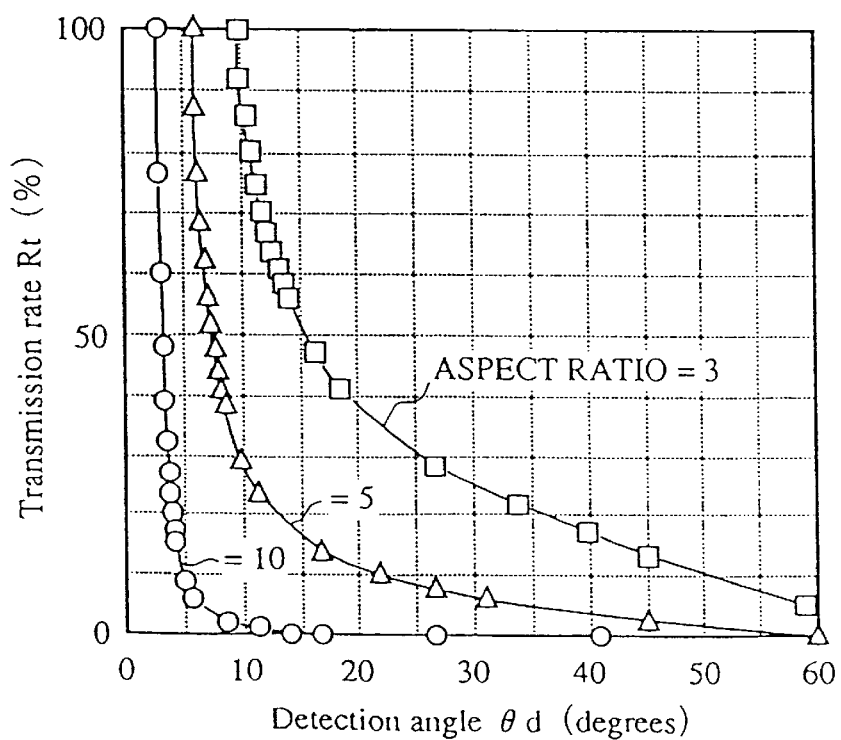

FIG. 15 shows how the transmission rate of an oxygen X-ray varies with changes in aspect ratio d/2a of a contact hole under the same conditions as those described above. It is obvious from the figure that, the smaller the aspect ratio d/2a, essentially the shorter the transmission distance, a distance in the sidewall of the contact hole traveled along by the oxygen X-ray which originates from an X-ray source on the bottom surface of the contact hole, penetrating the sidewall of the contact hole toward the detector 6. As a result, the transmission rate of the X-ray increases. Accordingly, when analyzing the bottom surface of a contact hole having a small aspect ratio, the analysis can then be carried out with a high degree of sensitivity by, for example, detecting all X-rays at angles of detection of smaller than 20 degrees from the center axis of the irradiated electron beam. It should be noted that, in the examples described above, the sidewall of the contact hole is made of a material having a property of letting an X-ray penetrate most easily. However, it is necessary to take every caution against the fact that, in the case of a hole sidewall made of an $SiO_2$ film or other materials, the transmission rate of the X-ray is decreased. From the explanation given above, it is obvious that, by installing an X-ray detector at an angle which allows X-rays passing through the sidewall of the contact hole to be also observed as well, in some cases, the quantity of the detected signal can be increased, enabling high-sensitivity analyses. Accordingly, the position for observing an X-ray in accordance with the present invention is not limited only to the range with upper limits determined by the angle $\theta$ which is defined that $\tan \theta$ is equal to a/d. Instead, the observation can be carried out at a position in a range of angles at which an X-ray emitted upward after passing through the sidewall of the contact hole can also be detected. None the less, it is desirable though to observe the X-ray at an angle smaller than 20 degrees.

By virtue of the present invention, an X-ray generated by application of an irradiated electron beam having low energy to the surface of a sample can be observed from a position in a direction close to the electron beam. Accordingly, qualitative and quantitative analyses of residue on the surface of the sample can be carried out with a high degree of sensitivity even for a sample having large surface steps without destructing the sample. As a result, the sample (for example, a wafer) can be returned back to the manufacturing process.

Embodiment 2

Figure 3:
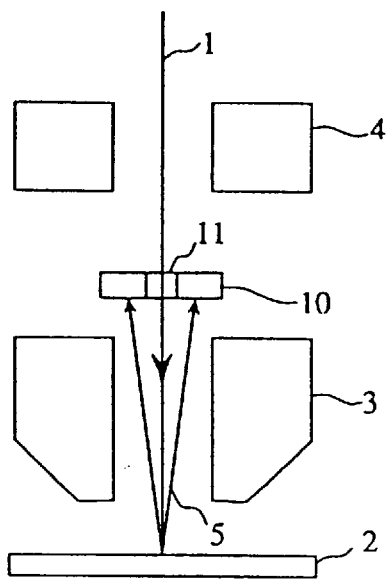
FIG. 3 is a cross-sectional model diagram showing a simplified configuration of another embodiment implementing an X-ray analysis apparatus in accordance with the present invention.

Another embodiment provided by the present invention is shown in FIG. 3. In this embodiment, an accelerated electron beam 1 passes through a through hole 11 at the center of a detector 10, which is installed between an objective lens 3 and a condenser lens 4. The irradiated electron beam 1 is then applied perpendicularly to the surface of a sample 2. A through hole 11 having a diameter ranging from about 0.1 to 5 mm will work. X-rays 5 generated by the application of the irradiated electron beam 1 are detected by the detector 10 to undergo energy analyses.

Since the shape of a detecting device employed in the detector 10 resembles a donut, the detection area of the detecting device can be enlarged in comparison with that of the detector 6 employed in the first embodiment. Speaking in concrete terms, in contrast with a detection area of merely 30 mm² in the case of the detector 6, the detector 10 can have a detection area of 150 mm², a value five times as much. As a result, a residue analysis can be carried out with a high degree of sensitivity in comparison with that of the first embodiment.

It should be noted, however, that the shape of the detector 10 does not necessarily have to resemble a donut as described above. Instead, a detector having another structure can be employed as a substitute as long as the detection area of its detecting device can be substantially increased. For example, a plurality of detectors 6 employed in the first embodiment are prepared and arranged to form a radial around the electron beam 1. As another alternative, the unit for accommodating the detector 6 in the housing 9 can be designed into a ring shape wherein a plurality of detecting devices are laid out to form a circular structure. An essential feature offered by this embodiment is the fact that the detection area of the detecting device is substantially enlarged without obstructing the electron beam 1.

As described above, since this embodiment allows the reception area of the detector to be enlarged in comparison with that of the first embodiment, it is possible to carry out a residue analysis with a high degree of sensitivity.

Embodiment 3

Figure 4:
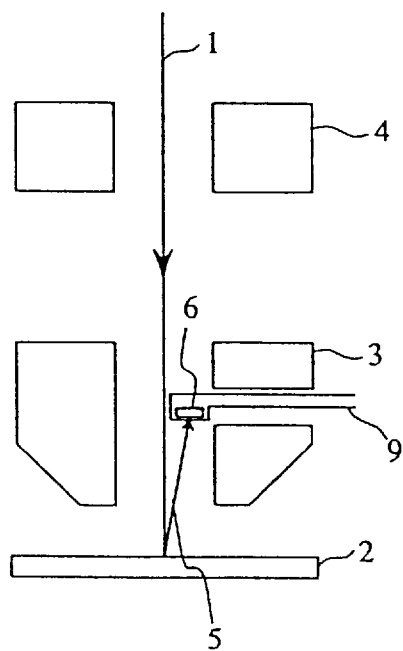
FIGS. 4, 5, 6 and 7 are cross-sectional model diagrams showing simplified configurations of still other embodiments each implementing an X-ray analyzing apparatus in accordance with the present invention.

A still further embodiment provided by the present invention is shown in FIG. 4. In this embodiment, a detector 6 having an energy analyzing function is installed in an internal space inside an objective lens 3.

In this embodiment, a detector 6 having the same structure as that of the first embodiment is employed for detecting an X-ray. However, a detector 10 having a coaxial donut-like structure like the one employed in the second embodiment can also be used by installing it in an internal space inside the objective lens 3.

In this embodiment, the detector 6 can be installed at a position close to the sample 2 in comparison with the previous first and second embodiments, allowing an X-ray detection signal with a high intensity to be obtained. As a result, a residual analysis can be performed with a higher degree of sensitivity.

Embodiment 4

Figure 5:
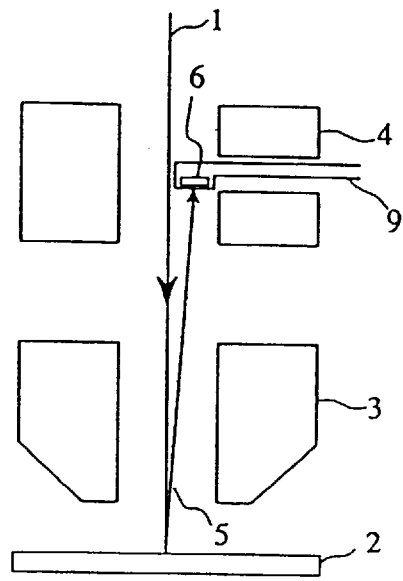

A still further embodiment provided by the present invention is shown in FIG. 5. In this embodiment, a detector 6 having an energy analyzing function is installed in an internal space inside a condenser lens 4.

In this embodiment, a detector 6 having the same structure as that of the first embodiment is employed for detecting an X-ray. However, a detector 10 having a coaxial structure like the one employed in the second embodiment can also be used by installing it in an internal space inside the condenser lens 4.

In this embodiment, the distance from the detector 6 to the surface of the sample 2 is long in comparison with the previous first to third embodiments. Accordingly, the intensity of the obtained X-ray detection signal is decreased slightly. With an increased distance from the detector 6 to the surface of the sample 2, however, an analysis of a sample with an angle $\theta$ smaller than that shown in FIG. 2, or a residue inside a fine hole with a smaller diameter 2a can thereby be carried out.

Embodiment 5

Figure 6:
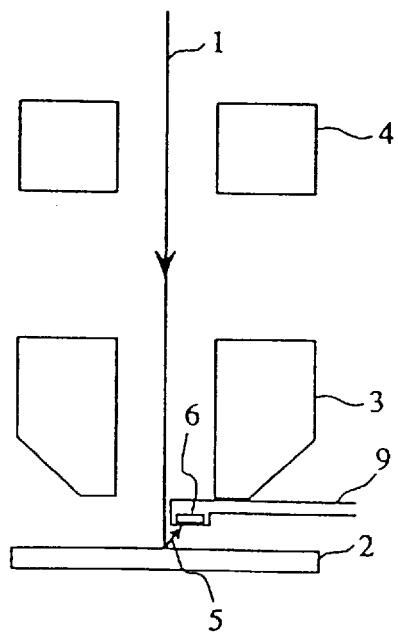

A still further embodiment provided by the present invention is shown in FIG. 6. In this embodiment, a detector 6 is provided below an objective lens 3.

In this embodiment, the distance from the detector 6 to the surface of the sample 2 can be shortened in comparison with the previous first to third embodiments. Accordingly, an X-ray generated from the surface of the sample 2 experiencing no attenuation can be detected. As a result, a residual analysis can be performed with a high degree of sensitivity in comparison with the first to fourth embodiments.

Embodiment 6

Figure 7:
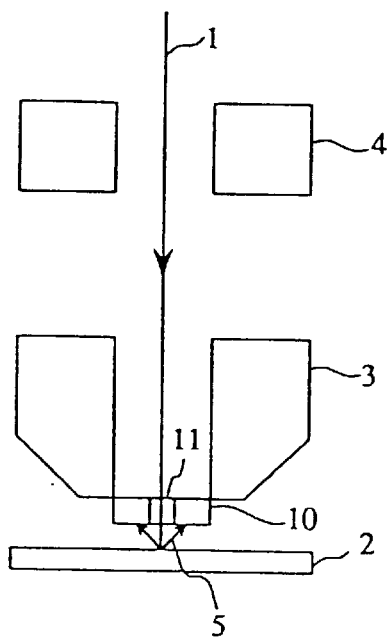

A still further embodiment provided by the present invention is shown in FIG. 7. In this embodiment, a donut-like X-ray detector 10 having a through hole 11 at the center thereof for passing through an irradiated electron beam 1 is provided below an objective lens 3.

Much like the fifth embodiment, the distance from the surface of the sample 2 to the detector 10 in this embodiment can be shortened and, on top of that, much like the second embodiment, the detection area of the detecting device can be enlarged. As a result, a residual analysis can be performed with a high degree of sensitivity in comparison with the first to fifth embodiments.

Embodiment 7

An analysis procedure for carrying out a quantitative analysis of the thickness of residue on the surface of a sample is explained through description of this embodiment.

First of all, the beam current of an electron beam 1 is measured by using a measurement means such as a Faraday-cup collector provided inside an analyzing apparatus. Even though the means for measuring the beam current does not have to be installed at a particularly prescribed position, it is desirable to provide the means on a sample holder for holding a sample 2. Then, the position of residue on the surface of the sample 2 to be analyzed is determined by means of a secondary-electron detector 8. Finally, a quantitative analysis of the residue thickness is carried out in accordance with the method adopted in one of the first to sixth embodiments.

In the analysis methods and apparatuses implemented by the first to sixth embodiments described so far, one of factors causing the accuracy of the residue-thickness analysis to deteriorate is variations in beam current of the electron beam 1 due to a variety of reasons. Since the magnitude of an X-ray 5 generated from the surface of the sample 2 is proportional to the current density of the irradiated electron beam, the magnitude of the generated X-ray varies with changes in beam current. Accordingly, the residue thickness cannot be measured accurately. In order to measure the residue thickness with a high degree of accuracy, it is thus necessary to clarify the relation between the current value of the electron beam and the detected-signal intensity of the X-ray 5. According to the measurement procedure of this embodiment, the detected-signal intensity of the X-ray 5 is measured after the measurement of the current value of the electron beam. Accordingly, information on the relation between the current value of the electron beam and the detected-signal intensity of the X-ray 5 can be obtained. As a result, the residue thickness can be measured with a high degree of accuracy by normalization (standardization) of the detected-signal intensity of the X-ray 5 with respect to the current value of the electron beam.

In the case of an analysis apparatus equipped with position-measuring (position-monitoring) unit, memory and a drive-control mechanism at a sample stage thereof, the position of the instrument for measuring the current of the electron beam and the position of an instrument for carrying out a quantitative analysis of the sample or a plurality of such quantitative-analysis positions whenever applicable are stored in the memory. By moving the sample stage to any arbitrary position at a high speed, the measurement of the electron-beam current and the analysis of the sample surface can be carried out alternately with a high degree of efficiency.

As described above, this embodiment allows information on the electron-beam current and the detected-signal intensity of the X-ray 5 to be obtained accurately and the residue thickness can hence be measured with a high degree of accuracy by normalization of the detected-signal intensity of the X-ray 5 with respect to the electron-beam current.

Embodiment 8

An analysis procedure for carrying out a quantitative analysis of the thickness of residue on the surface of a sample which is different from that of the seventh embodiment is explained through description of this embodiment.

First of all, the intensity of an X-ray generated from a reference sample, the material property of which is known in advance, is measured. Even though the reference sample does not have to be put at a particularly prescribed position, it is desirable to place the reference sample on a sample holder for holding a sample 2. Then, the position of residue on the surface of the sample 2 to be analyzed is determined by means of a secondary-electron detector 8. Finally, a quantitative analysis of the residue thickness is carried out in accordance with the method adopted in one of the first to sixth embodiments.

The seventh embodiment described above adopts an analysis method by normalization of the detected-signal intensity of the X-ray 5 with respect to the electron-beam current. On the other hand, according to this embodiment, the analysis method is implemented by normalization of the detected-signal intensity of the X-ray 5 with respect to the detected-signal intensity of the X-ray 5 generated by the reference sample. Also with the method of this embodiment, the same effects as those of the seventh embodiment can be obtained as well.

Embodiment 9

Measurement of the removed thickness of an underneath-layer material existing on the surface of the bottom of a hole resulting from a patterning process of a contact hole in a semiconductor manufacturing process is explained through description of this embodiment. In the measurement, the method of one of the first to eight embodiment is adopted.

Figure 8:
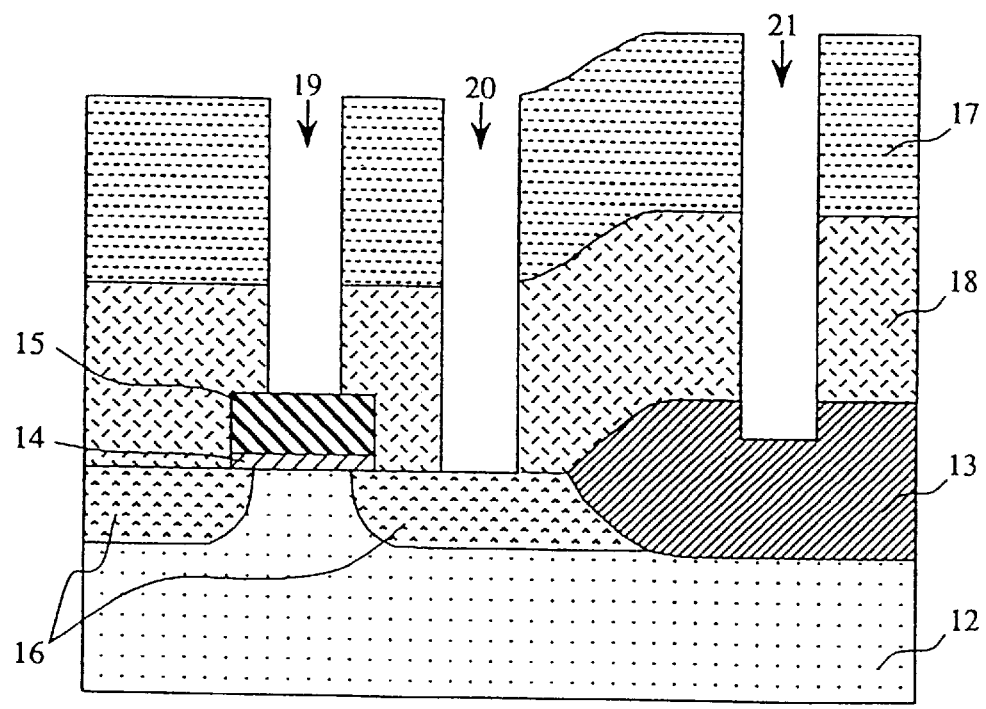
FIG. 8 is a cross-sectional diagram showing a typical structure of a contact hole in a semiconductor device.

FIG. 8 is a diagram showing a cross section of a contact hole of a semiconductor device. Reference numeral 12 shown in the figure is a silicon substrate whereas reference numeral 13 denotes an insulating film for element isolation. Reference numerals 14 and 15 are a gate insulating film and a gate electrode respectively. Reference numeral 16 denotes a source and drain high-concentration layer whereas reference numeral 17 is a resist layer. Reference numeral 18 denotes an interlayer insulating film whereas reference numerals 19 and 20 are contact holes. Reference numeral 21 is a contact hole provided for evaluating the removed thickness of an underneath-layer material, the insulating film 13 for element isolation.

This embodiment is characterized in that a contact hole used for evaluating the removed thickness of the underneath-layer material is formed on a semiconductor device. The method adopted in one of the first to eighth embodiments is used for measuring the residue thickness of the element-isolation insulating film 13 existing on the surface of the bottom of the contact hole 21. From the difference between the original thickness of the element-isolation insulating film 13 before the patterning of the contact hole 21 and the thickness remaining after the contact-hole patterning, the removed thickness of the underneath-layer material can be derived.

Figure 9:
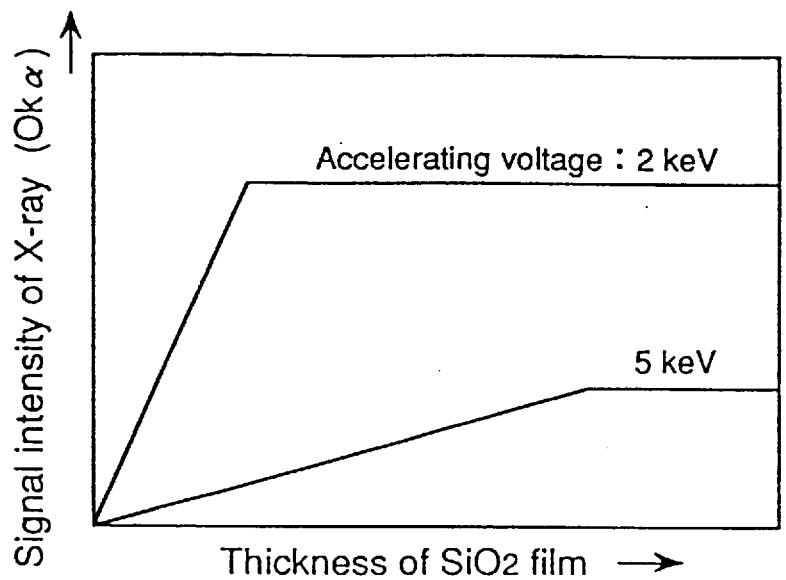
FIG. 9 is a diagram showing the dependence of the signal intensity of an X-ray on the $SiO_2$-film thickness.

A point to consider in the measurement of the residue thickness of the element-isolation insulating material 13 is that it is necessary to properly set the accelerating voltage of the electron beam according to the residue thickness. Dependence of the signal intensity of the X-ray on the thickness of the insulating film (the $SiO_2$ film) is shown in FIG. 9. It is obvious from the figure that, for an accelerating voltage of 2 keV, the signal intensity of the X-ray is high but, on the other hand, for relatively high values of the $SiO_2$-film thickness, the signal intensity of the X-ray is saturated, making it impossible to measure the thickness of the $SiO_2$ film. For an accelerating voltage of 5 keV, on the other hand, the signal intensity of the X-ray is low but the thickness of a thicker $SiO_2$ film can be measured. The fact that, the lower the accelerating voltage, the higher the signal intensity of the X-ray, can be attributed to the fact that the total amount of X-ray is a function of accelerating voltage. At an accelerating voltage of about three times the energy of the X-ray (about 0.5 keV in the case of an OKα X-ray), the total amount of X-ray reaches a maximum value. Refer to 'Optical Systems for Soft X-rays', written by A. G. Michette, Prenum Press, New York, 1986, pp. 22. It should be noted that as the accelerating voltage is raised to a value of higher than 5 keV, the signal intensity of the X-ray is decreased considerably, making it impossible to measure the residue thickness. The fact that, the higher the accelerating voltage, the more possible the measurement of the thickness of the $SiO_2$ film, is attributed to the fact that, the higher the accelerating voltage, the deeper the projection range of the electron into the film. For the reasons described above, it is necessary to lower the accelerating voltage to 2 keV in the case of a thin $SiO_2$ film and to raise the accelerating voltage to 5 keV in the case of a thick $SiO_2$ film.

As described above, according to this embodiment, a contact hole is formed for evaluating the removed thickness of an underneath-layer material on a semiconductor device. By measuring the residue thickness of the underneath-layer material on the surface of the bottom of the contact hole at an appropriate accelerating voltage, inline evaluation can be carried out for the removed thickness of the underneath-layer material.

Embodiment 10

A method for determining whether a contact hole in a semiconductor manufacturing process is a complete opening or not is described through this embodiment. In this embodiment, the method of one of the first to eighth embodiments is adopted.

Figure 16:
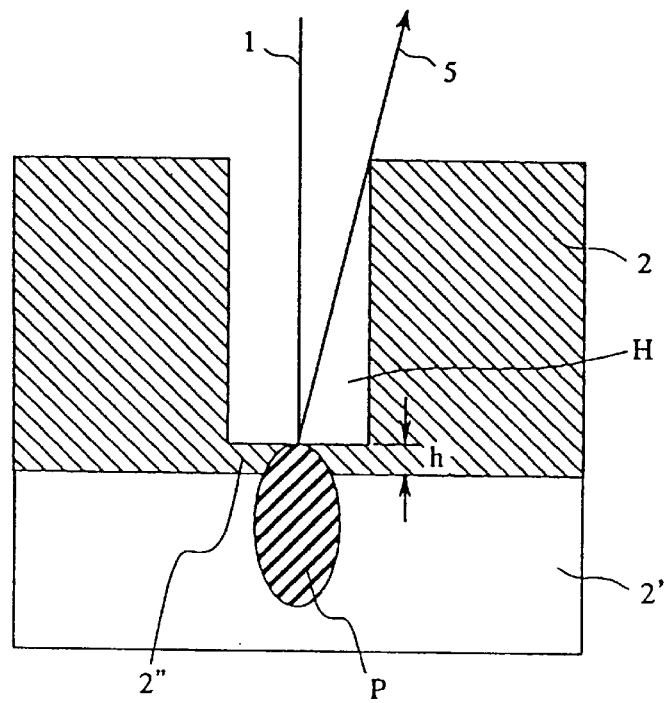
FIGS. 16 and 18 are cross-sectional model diagrams used for explaining techniques of judging the opening state of a contact hole by using an X-ray analysis method provided by the present invention.
Figure 17:
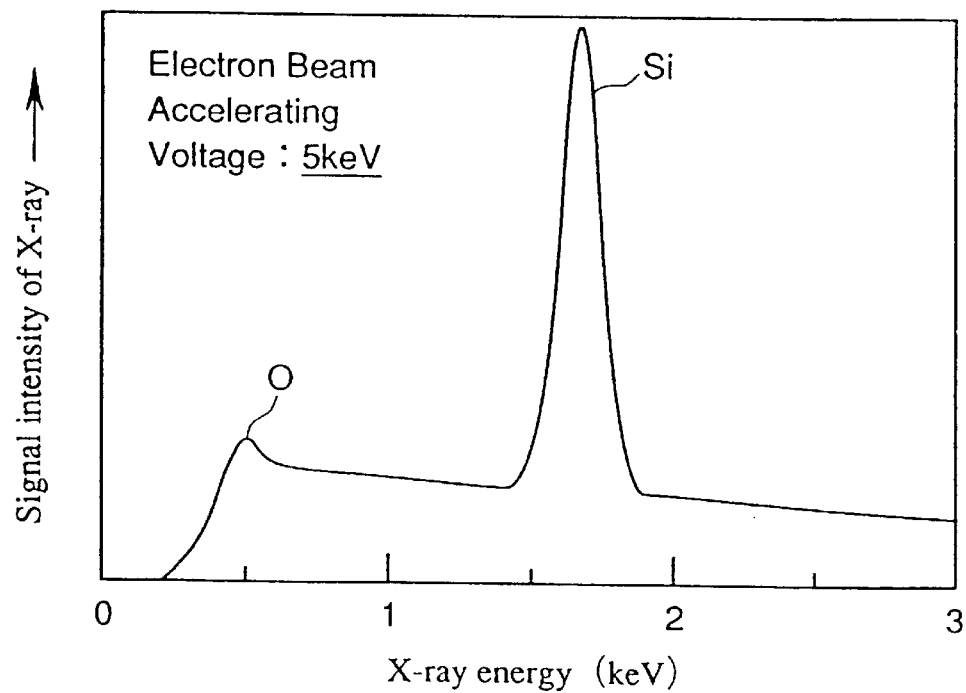
FIGS. 17 and 19 are charts representing spectra of X-rays detected by the techniques shown in FIGS. 16 and 18 respectively.

FIG. 16 shows a state in which an analysis of $SiO_2$ residue existing on the surface of the bottom of a contact hole in a semiconductor device is carried out. As shown in the figure, a contact hole H is formed in an $SiO_2$ film 2 provided on a silicon substrate 2'. An $SiO_2$ residue 2" exists on the bottom of the contact hole H. An irradiated electron beam 1 with an accelerated voltage of 5 keV is applied to the $SiO_2$ residue 2". In the case of an $SiO_2$ residue 2" with a small thickness h, the electron beam 1 with an accelerated voltage of 5 keV allows irradiated electrons to penetrate the $SiO_2$ residue 2" with ease, arriving at the silicon substrate 2'. Accordingly, an area P generating X-rays 5 is distributed to deep locations in the silicon substrate 2'. In this case, the spectrum of the generated X-rays 5 is shown in FIG. 17. Since the X-ray generating area P has a portion in the silicon substrate 2' larger than a portion in the $SiO_2$ residue 2", the signal intensity of the Si (silicon) X-ray is high but, on the other hand, the signal intensity of the O (oxygen) X-ray from the $SiO_2$ residue 2" is low. For this reason, it is necessary to prolong the measurement time in order to determine the existence/non-existence of a thin $SiO_2$ residue. In addition, for a high accelerating voltage of 5 keV, on the other hand, the amount of noise caused by the so-called 'bremsstrahlung' (braking radiation) is large and X-rays generated from the sidewall (which is also an $SiO_2$ film) of the contact hole by electrons reflected from the surface of the bottom of the hole are also inevitably detected, lowering the precision of the analysis.

Figure 18:
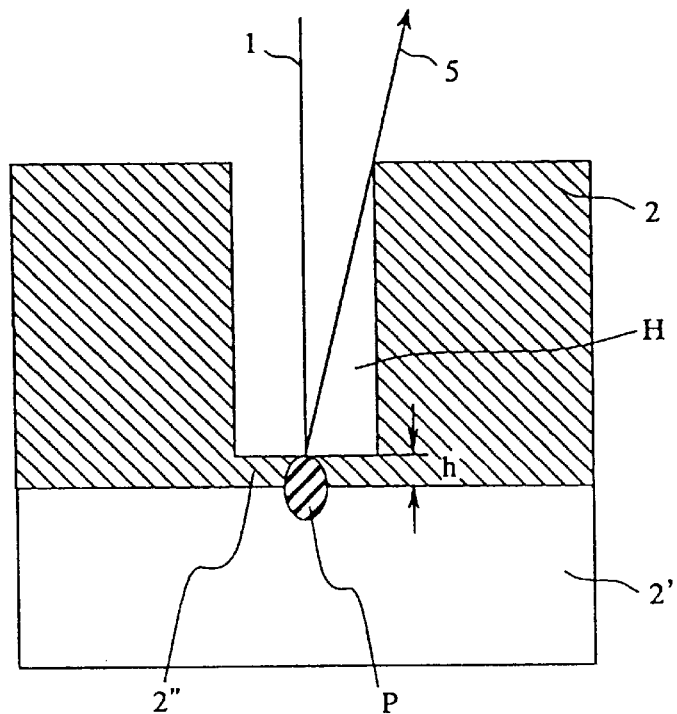
Figure 19:
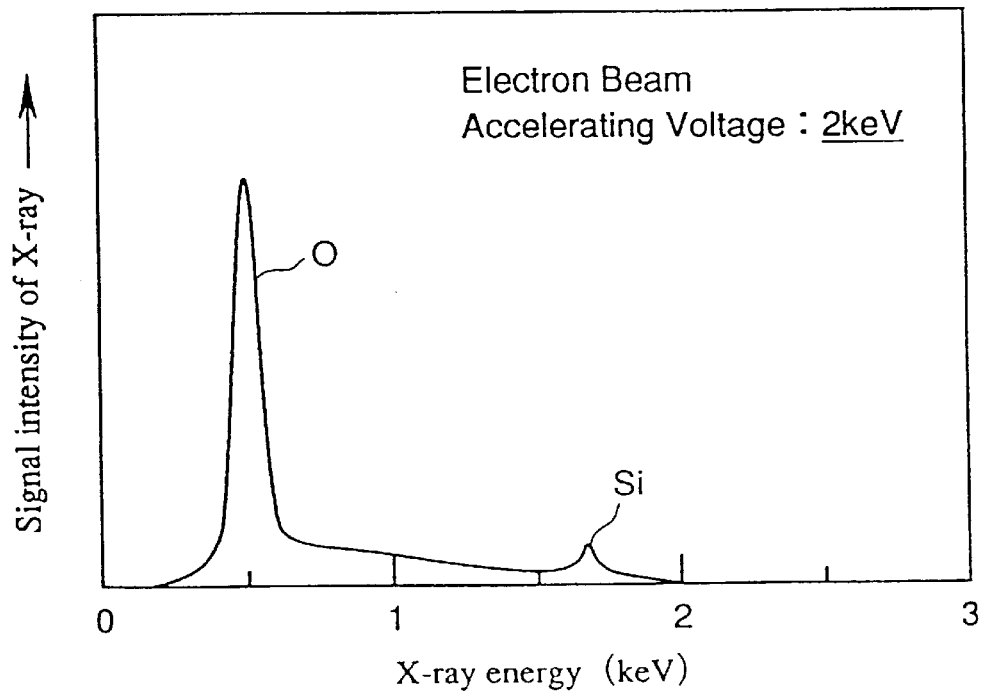

In the case of an electron beam with a low accelerating voltage of 2 keV, on the other hand, the distribution of the area P generating X-rays in the silicon substrate 2' is small in comparison with that for an accelerating voltage of 5 keV described above as shown in FIG. 18. In this case, the spectrum of the generated X-rays is shown in FIG. 19. As described in the above ninth embodiment, the signal intensity of the O (oxygen) X-ray reaches a maximum value at an accelerating voltage of 1.5 to 2 keV. In this case, the signal intensity of the O (oxygen) X-ray is therefore high in comparison with that shown in FIG. 17. In the case of an accelerating voltage of 2 keV, on the other hand, it is difficult to excite the Si (silicon) X-ray and, in addition, the distribution of the X-ray generating area P in the silicon substrate 2' is small. Accordingly, the signal intensity of the Si (silicon) X-ray is low. On top of that, at a low accelerating voltage, the generation of reflected electrons and noise caused by the bremsstrahlung is low, allowing the amount of background noise to be reduced and the number of erroneous signals coming from the sidewall of the contact hole to be decreased. As a result, an analysis of an oxygen X-ray can be carried out with a high degree of sensitivity. For those reasons, it is possible to determine the existence/non-existence of $SiO_2$ residue on the surface of the bottom of the contact hole.

As described above, this embodiment allows an X-ray generated by light elements such as C (carbon) and O (oxygen) to be analyzed with a high degree of sensitivity if the X-ray analysis is carried out by accelerating an irradiated electron beam using a low accelerating voltage of 2 keV. As a result, it is possible to determine whether the opening of a contact hole is complete or not in a short period of time.

Embodiment 11

Figure 10:
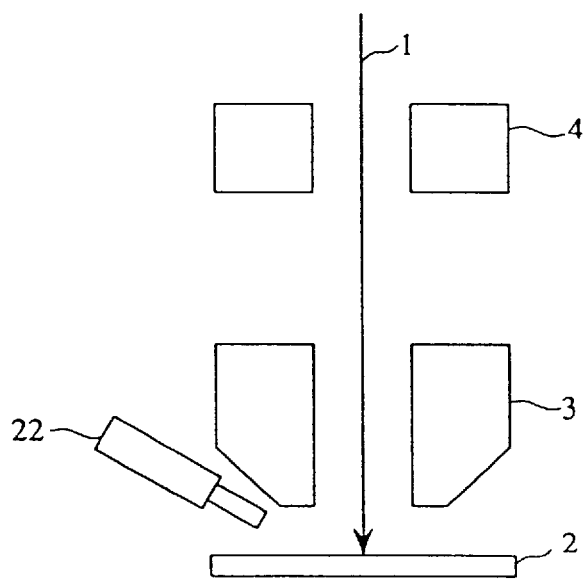
FIG. 10 is a cross-sectional model diagram showing a simplified configuration of a still further embodiment implementing an X-ray analyzing apparatus in accordance with the present invention.

A still further embodiment provided by the present invention is shown in FIG. 10. This embodiment is an example wherein a means for heating the surface of a sample 2 is provided. In this embodiment, an area on the surface of the sample 2 including a location, to which an irradiated electron beam 1 is applied, is heated while the irradiated electron beam 1 is being applied to the location. In the mean time, residue on the surface of a sample 2 is analyzed by using the method adopted by one of the first to seventh embodiments. As a means for heating the surface of the sample 2, a semiconductor laser 22 having a wavelength of 800 nm is used for applying an irradiated laser light to the surface of the sample 2. In this way, an area on the surface of the sample 2 with a diameter of about 5 mm, to which the irradiated laser light is applied, is heated to a temperature of 200° C.

As an irradiated electron beam 1 is applied to the surface of the sample 2, a carbon compound is adhered to an area on the surface of the sample 2 which the electron beam 1 is applied to. If the intensity of an X-ray generated by the residue is low due to, for example, a small residue thickness, the sensitivity of analysis observed during the analysis of the residue on the surface of the sample 2 is low due to an effect of the adhered carbon compound. In order to analyze thin residue with a high degree of sensitivity, it is thus necessary to prevent a carbon compound from being adhered to the surface of the sample 2 due to the application of the irradiated electron beam thereto. By heating the surface of the sample 2 to a temperature of 200° C. in accordance with this embodiment, the adherence of a carbon compound to the surface of the sample 2 can be avoided, allowing the analysis of the residue to be carried out with a high degree of sensitivity even if the intensity of an X-ray generated from the residue is low.

In this embodiment, a semiconductor laser is used as a means for heating the surface of a sample. It should be noted, however, that the means for heating the surface of a sample is not necessarily limited to a semiconductor layer. Any heating means can be used as long as it can substantially heat the surface of a sample. Note that, in order to prevent a carbon compound from being adhered to the surface of a sample, it is necessary to set the heating temperature of the surface of a sample at a value higher than 100° C.

A carbon compound can be prevented from being adhered to the surface of a sample by a technique other than heating the sample. The means for generating an X-ray by application of an irradiated electron beam and the means for analyzing the generated X-ray are installed in a vacuum chamber. By setting the degree of vacuum in the vacuum chamber at $1\times10^{-6}$ torr or lower, the amount of the carbon compound existing in the vacuum chamber can be reduced, allowing the carbon compound to be prevented from being adhered to the surface of the sample.

As described above, the carbon compound can be prevented from being adhered to the surface of the sample by heating the surface of the sample in accordance with this embodiment, allowing residue to be measured with a high degree of sensitivity.

Embodiment 12

Figure 11:
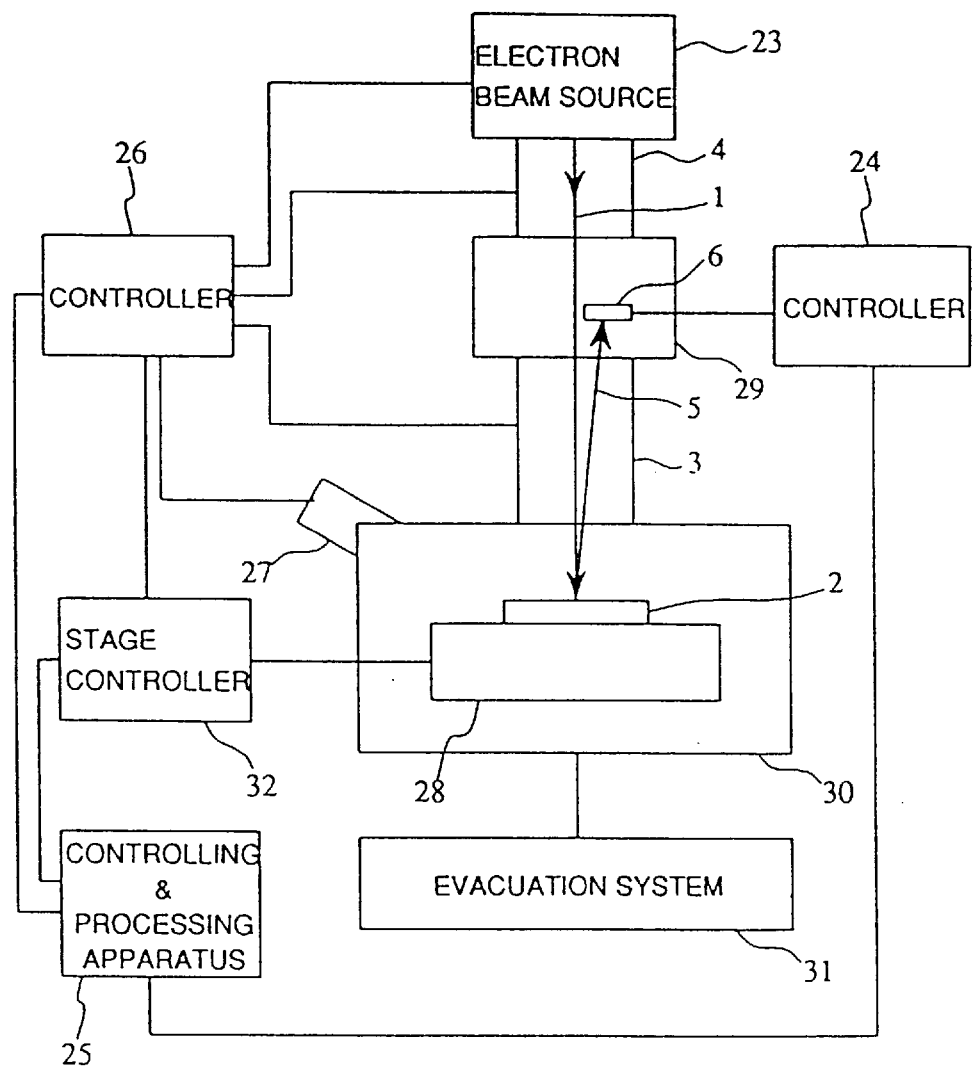
FIG. 11 is a cross-sectional model diagram showing a simplified configuration of a still further embodiment implementing an X-ray analyzing apparatus in accordance with the present invention.

The methods of analysis and apparatuses implemented by the first to tenth embodiments can be provided with additional functions to widen the generality as analysis apparatuses. As additional functions, a function for measuring dimensions of a fine pattern (or a length measuring function) and a function for accelerating an electron beam to a high speed can be thought of. An embodiment that includes these additional functions is shown in FIG. 11. As shown in the figure, accelerated electron beam 1 irradiated from an electron-beam source 23 is converged by a condenser lens 4 and an objective lens 3 before being applied to the surface of a sample 2 placed in a sample chamber 30. An X-ray 5 generated from the surface of the sample 2 by the application of the irradiated electron beam 1 thereto is detected by an X-ray detector 6 which has an energy analyzing function and is installed in a vacuum chamber 29. The X-ray detector 6 is installed at a position in a direction close to the center axis of the electron beam 1 when seen from a position on the surface of the sample 2 to which the irradiated electron beam 1 is applied. An X-ray detection signal output by the X-ray detector 6 is processed by a controller 24 before being transmitted to a controlling and processing apparatus 25 where analysis results are displayed.

In this embodiment, the accelerating energy of the electron beam 1 can be freely varied between 0.1 to 200 keV by using a controlling apparatus 26. In the case of an electron beam 1 with a low accelerating energy, a qualitative and quantitative analysis of residue on the surface of the sample 2 can be carried out by detecting an X-ray generated from the surface of the sample 2 as described so far. For an electron beam 1 with a high accelerating energy of greater than 50 keV, on the other hand, an image on the surface of the sample 2 can be obtained by detecting secondary and reflected electrons coming from the surface of the sample 2. In particular, an electron with a high accelerating energy also has a high power to penetrate a substance. Thus, a shape inside a fine hole, for example, can be observed by detecting reflected electrons. These secondary and reflected electrons are detected by using an electron detector 27. As a result, not only can a shape inside the fine hole be observed, but it is also possible to identify the type of an element making up the shape or the like.

The apparatus shown in FIG. 11 has an additional function for measuring the length of a fine pattern. Dimensions of a fine pattern are measured typically as described below. The surface of the sample 2 is scanned by the electron beam 1 by controlling a deflector provided in an objective lens 3 by means of the controlling apparatus 26. Secondary electrons generated from the surface of the sample 2 are detected to display a secondary-electron image of the surface of the sample 2 on a display screen of the controlling and processing apparatus 25. In this case, an electron beam 1 having an accelerating energy of smaller than 5 keV will work. A fine pattern, the dimensions of which are to be measured, is specified while the secondary-electron image is being observed. In this way, information on the dimensions of the fine pattern can be obtained from the amounts of deflection of the electron beam 1. Instead of deflecting the electron beam 1, a sample stage 28 can be moved by a stage controlling apparatus 32. The dimensions of the fine pattern can then be found as well from the amount of the movement.

It should be noted that the inside of an electron irradiating system for applying an irradiated electron beam 1 to the surface of the sample 2 and generating X-rays as well as secondary and reflected electrons therefrom and the inside of a detecting system for detecting the generated X-rays as well as secondary and reflected electrons are evacuated into a highly vacuum state by using an evacuating system 31.

As described above, this embodiment allows the shape of residue to be observed and dimensions of a fine hole to be measured in addition to a qualitative and quantitative analysis of the residue. As a result, more complete information on a fine pattern can be obtained.

Embodiment 13

This embodiment implements a method for forming a judgment on the state of a fine contact hole created on the surface of a semiconductor wafer in a process of manufacturing a semiconductor device (a MOS-structure LSI) in an even shorter time, that is, a judgment as to whether or not the fine contact hole is an opening or a non-opening, and the configuration of an apparatus suitable for implementation of the method.

Figure 21:
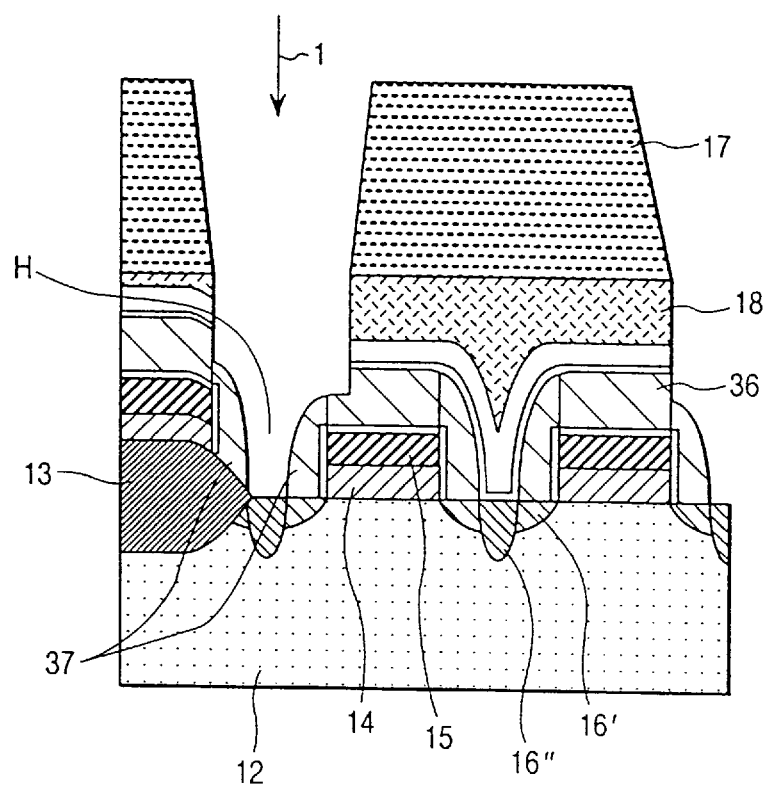
FIG. 21 is a diagram showing a cross section of an embodiment implementing an LSI using a fine MOS structure.

FIG. 21 is a diagram showing a cross section of an embodiment implementing an LSI using a fine MOS structure. Reference numerals 12 and 13 shown in the figure are a silicon substrate and an insulation layer for isolating elements from each other respectively. Reference numeral 14 is a gate insulation layer of a MOS transistor, a kind of oxide layer, and reference numeral 15 is a gate electrode. Reference numerals 16' and 16" each denote an impurity area for creating a source and a drain. To be more specific, reference numeral 16' is an area with a low concentration of impurities while reference numeral 16" is an area with a high concentration of impurities. Reference numeral 17 and 18 denote a resist film to be formed into a pattern and an insulation film between layers respectively which is referred to hereafter as an interlayer insulation film. Reference numeral 36 is an insulation film for protecting the gate electrode 15 and reference numeral 37 denotes a side-wall insulation film for creating an LDD (Lightly Doped Drain) structure. In this fine MOS structure, the low-concentration impurity area 16' is created by making use of the side-wall insulation film 37 in order to reduce an electric field existing between the source and the drain of the MOS transistor. In addition, the contact hole H in this high-integration fine MOS structure corresponding to the contact hole 20 shown in FIG. 8 is formed to be self-aligned also by making use of the side-wall insulation layer 37. To put it in detail, the interlayer insulation film 18 is etched by using a condition of a resulting difference in etching speed between the interlayer insulation film 18 and the side-wall insulation film 37 (with the speed of the former 18 higher than the speed of the latter) with the resist-film pattern 17 used as a mask. By adopting such a contact-hole forming method, it is possible to form a contact hole H having dimensions which are extremely small from the standpoint of a self-aligned characteristic with respect to an infinitesimal gap formed between the side-wall insulation films 37 of two MOS transistors adjacent to each other. In the case in which the infinitesimal gap formed between the sidewall insulation films 37 of two MOS transistors adjacent to each other is 0.15 microns and the width (or the thickness) of both the side-wall insulation films is 0.05 microns, an extremely fine contact hole H having a width of merely 0.05 microns is obtained.

When forming a judgment as to whether or not the fine contact hole H formed by the process described above is an opening or a non-opening by analyzing insulation-film residue left at the opening bottom of the hole using the analysis method provided by the present invention, it is necessary to sufficiently take an effect of the side-wall insulation film on results of the analysis into consideration. In this embodiment, by comparing results of analyses conducted on a plurality of contact holes, it is possible to form such a judgment with the effect of the side-wall insulation film eliminated in such a case.

Figure 20:
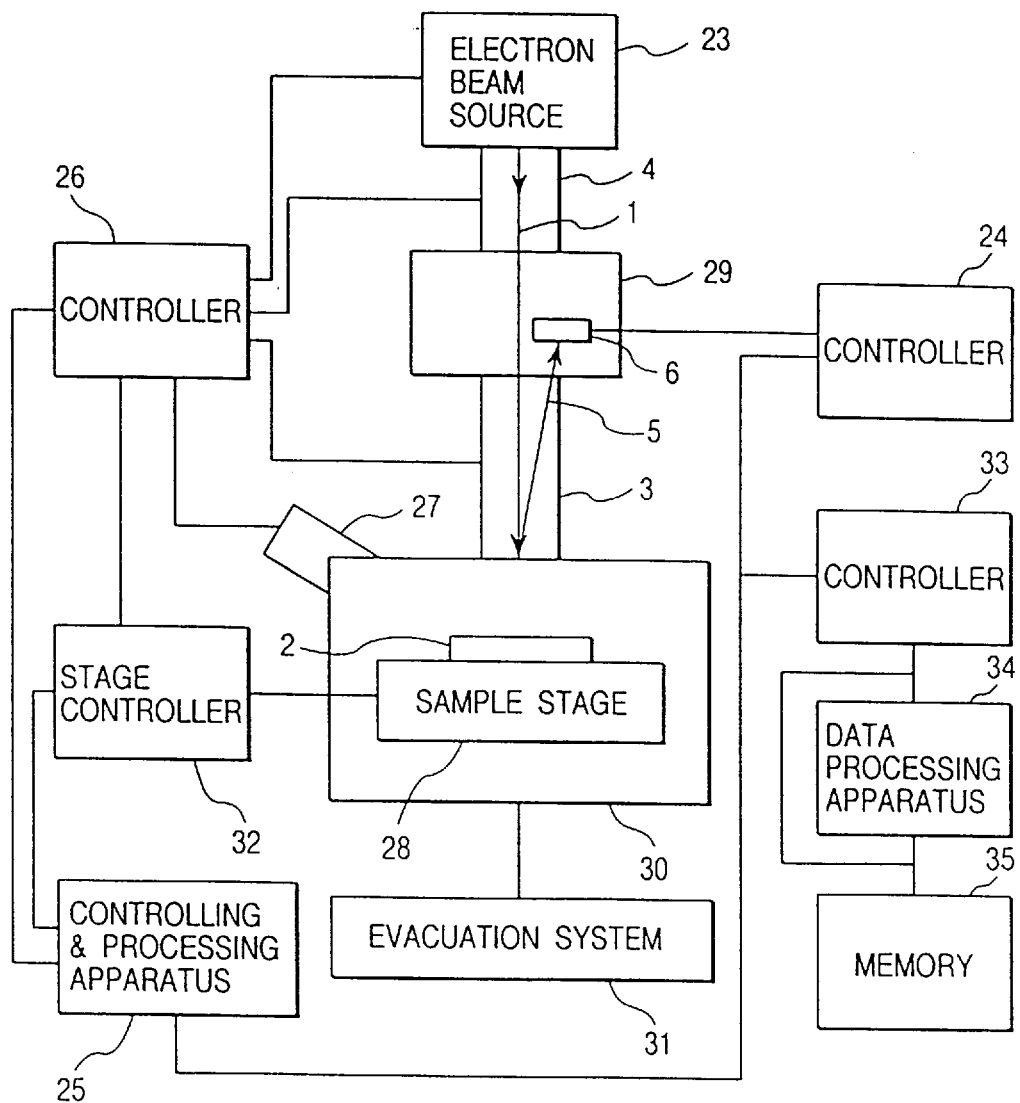
FIG. 20 is a diagram showing an overall configuration of an X-ray analyzing apparatus implemented by a still further embodiment of the present invention.

First of all, the configuration of an X-ray analyzing apparatus used in this embodiment is explained by referring to FIG. 20. Reference numerals 1 to 32 shown in this figure denote the same things as those shown in FIG. 11. In the case of the X-ray analyzing apparatus shown in FIG. 20, however, a controller 33, a data processing apparatus 34 and a memory 35 are newly added. As shown in the figure, the controller 33 receives necessary information from the controller 25 which receives signals from the stage controller 32 and the controller 26 employed in the electronic optical system. The controller 33 produces information on position adjustment and sample-stage inclination for adjusting the position of a sample and supplies analysis data for another contact hole or a plurality of other contact holes subjected to comparison to the memory 35 to be stored therein. It should be noted that analysis data to be compared is not limited to data obtained from the same sample. The data processing apparatus 34 compares analysis data obtained as a result of an analysis of the opening bottom of a contact hole being analyzed on the basis of information obtained from the controller 33 with analysis data of another contact hole stored in the memory 35 in advance to find the difference between them. If the difference is found greater than a predetermined value, the data processing apparatus 34 forms a judgment that one of the contact holes is an opening (or a non-opening) while the other is a non-opening (or an opening). In this case, if another method has been used for assuring or inferring that the open state of the other contact hole is good, the contact hole subjected to the analysis can be verified and judged to be a non-opening. While a step movement of the stage 28 is being repeated, pieces of analysis data of a plurality of contact holes having identical structures formed on the surface of a sample are acquired sequentially one piece after another to be judged by comparison. In this way, information on distribution of the open or unopen state of contact holes formed on the surface of the sample can also be obtained as well. In addition, in a case where there are a number of contact holes subjected to an analysis on the surface of a sample, it is possible to reap an effect that the time required for the analysis can be shortened.

A procedure for forming a judgment by comparison as to whether a fine contact hole is an opening or a non-opening as described above is carried out as follows:

(1) First of all, a sample 2 subjected to an analysis is set on a sample stage 28 shown in FIG. 20. It should be noted that, by a sample, a semiconductor wafer in a process of manufacturing a semiconductor device is meant. The sample stage 28 is then positioned so as to move a first contact hole on the surface of the sample 2 subjected to the analysis to an analysis location on the optical axis of a irradiated electron beam.

(2) With the first contact hole placed at the analysis location, the coordinates of the position of the sample stage are stored in the memory 35.

(3) An electron beam is irradiated to the first contact hole and the circumference thereof. Subsequently, secondary electrons or reflected electrons coming from the surface of the sample 2 are detected by the detector 27 for generating a secondary-electron image signal or a reflected-electron image signal. The acquired secondary-electron image signal or a reflected-electron image signal is then stored in the memory 35.

(4) A finely converged electron beam is irradiated to the opening bottom of the first contact hole and a characteristic X-ray emitted from the opening bottom is detected by the detector 6 in order to analyze elements of a substance existing at the opening bottom.

(5) Results of the analysis of the opening bottom of the first contact hole are stored in the memory 35.

(6) The sample stage 28 is moved by a distance between the first contact hole and a second contact hole stored in the memory 35 in advance in order to move the second contact hole on the surface of the sample 2 subjected to the analysis to the analysis location.

(7) An electron beam is irradiated to the second contact hole and the circumference thereof. Subsequently, secondary electrons or reflected electrons coming from the surface of the sample 2 are detected by the detector 27. The acquired secondary-electron image signal or reflected-electron image signal of the second contact hole is then compared with the secondary-electron image signal or a reflected-electron image signal of the first contact hole already stored in the memory 35. The sample stage 28 is then moved by a distance corresponding to a positional discrepancy between the two images in order to correct the position of the sample stage 28.

(8) An electron beam is irradiated to the second contact hole and the circumference thereof. Subsequently, secondary electrons or reflected electrons coming from the surface of the sample 2 are detected by the detector 27. The acquired secondary-electron image signal or reflected-electron image signal is then stored in the memory 35. If necessary, the secondary-electron image signal or the reflected-electron image signal of the first contact hole is deleted from the memory 35.

(9) A finely converged electron beam is irradiated to the opening bottom of the second contact hole and a characteristic X-ray emitted from the opening bottom is detected by the detector 6 in order to analyze elements of a substance existing at the opening bottom. Results of the analysis of the opening bottom of the second contact hole are stored in the memory 35.

(10) The sample stage 28 is moved by a distance between the second contact hole and a third contact hole stored in the memory 35 in advance in order to move the third contact hole on the surface of the sample 2 subjected to the analysis to the analysis location.

(11) An electron beam is irradiated to the third contact hole and the circumference thereof. Subsequently, secondary electrons or reflected electrons coming from the surface of the sample 2 are detected by the detector 27. The acquired secondary-electron image signal or reflected-electron image signal of the third contact hole is then compared with the secondary-electron image signal or a reflected-electron image signal of the second contact hole already stored in the memory 35. The sample stage 28 is then moved by a distance corresponding to a positional discrepancy between the two images in order to correct the position of the sample stage 28.

(12) An electron beam is irradiated to the third contact hole and the circumference thereof. Subsequently, secondary electrons or reflected electrons coming from the surface of the sample 2 are detected by the detector 27. The acquired secondary-electron image signal or reflected-electron image signal is then stored in the memory 35. If necessary, the secondary-electron image signal or the reflected-electron image signal of the second contact hole is deleted from the memory 35.

(13) A finely converged electron beam is irradiated to the opening bottom of the third contact hole and a characteristic X-ray emitted from the opening bottom is detected by the detector 6 in order to analyze elements of a substance existing at the opening bottom. Results of the analysis of the opening bottom of the third contact hole are stored in the memory 35.

(14) Results of the analysis of the opening bottoms of the first, second and third contact holes are read out from the memory 35 and compared with each other by the data processing apparatus 34 to form a judgment as to whether or not there are substantial differences among the analysis results by finding out whether or not the differences among the analysis results are greater than a predetermined fixed threshold value.

(15) An identification code is appended to each contact-hole analysis data so that a contact hole with contact-hole analysis data judged at the step (14) to be different from the contact-hole analysis data of the first contact hole can be distinguished from a contact hole with contact-hole analysis data judged at the step (14) to be the same as the contact-hole analysis data of the first contact hole. The contact-hole analysis data of the first contact hole is referred to hereafter as reference contact-hole analysis data.

(16) If necessary, the secondary-electron image signal or the reflected-electron image signal of the third contact hole is deleted from the memory 35.

(17) The steps (1) to (16) are repeated till the analyses, comparisons and judgments for all other contact holes are completed.

(18) As the analyses, comparisons and judgments for all contact holes are completed, remove the sample 2 from the sample stage 28.

(19) Information on the positions of the contact holes on the surface of the sample 2 and the identification code appended to each contact-hole analysis data are output typically to a printer or a display unit by showing association of the positions with the identification codes.

(20) Data output at the step (19) is examined in order to form a judgment as to whether each contact hole is an opening or a non-opening. If it is assumed that the pieces of contact-hole analysis data include a piece of contact-hole analysis data of a contact hole which has been assured or inferred in advance to be a good opening, a contact hole having contact-hole analysis data with an identification code indicating that the contact-hole analysis data has been judged to be substantially the same as the contact-hole analysis data of the contact hole, which has been assured or inferred in advance to be a good opening, can be readily judged to be a good opening. For this reason, the first contact hole analyzed at the steps (4) and (5), the second contact hole analyzed at the step (9) or even the third contact hole analyzed at the step (13) can be selected as a contact hole assured to be a good opening in advance. Analysis data of the contact hole selected as a contact hole assured to be a good opening in advance is then stored in the memory 35 as reference contact-hole analysis data cited at the step (15).

It should be noted that the whole judgment procedure described above or part of it can be implemented as a program which is capable of automatically forming a judgment as to whether or not the opening state of each of contact holes subjected to the examination according to the procedure is good.

In addition, it should be noted that, while the present invention has been described with reference to an embodiment wherein the X-ray analysis method provided by the present invention is applied to an inspection of the opening states of fine contact holes of a semiconductor device, the description is not to be construed in a limiting sense. That is to say, the X-ray analysis method provided by the present invention can also be applied to an inspection of the opening states of fine holes having identical fine structures in a micromachine.

The present invention has been explained so far by describing a variety of embodiments. In order to detect an X-ray more effectively, means for finely adjusting the positions of an optical element and a detector are required. Even though these adjusting means are not shown in the figures, position adjusting tremor structures can be installed if necessary. In addition, it is needless to say that combinations of any of the embodiments cited above are also within the scope of the present invention. Furthermore, most of the means required for generating and measuring X-rays are installed in vacuum chambers even though they are not described in the explanations of the embodiments. It should be noted that, in case only few X-rays are absorbed by particles in the air, the sample can be put in a low-vacuum state.

It is obvious from the above description that, by virtue of the present invention, an X-ray generated from residue existing on the surface of a sample by the application of an irradiated and converged electron beam to the surface of the sample can be observed from a position in a direction close to the electron beam. As a result, a qualitative and quantitative analysis can be carried out on residue on the surface of a sample with large steps such as contact holes, to say nothing of a sample with small steps. On top of that, the analysis is not destructive, allowing the sample to be returned back to the manufacturing process after the analysis.

It is further understood by those skilled in the art that the foregoing description is no more than description of preferred embodiments of the disclosed method and apparatus and, therefore, a variety of changes and modifications may be made to the present invention without departing from the spirit and the scope thereof.

What is claimed is:

1. A method for inspecting opening states of a plurality of fine holes with identical structures formed on the surface of a sample, said method comprising the steps of:

(1) irradiating a finely converged electron beam into a first fine hole of said fine holes, observing an X-ray emitted from the inside of said first fine hole due to the irradiation of said electron beam in order to carry out an element analysis of a residue substance existing at the opening bottom of said first fine hole and storing first analysis data resulting from said element analysis into a memory;

(2) irradiating a finely converged electron beam into a second fine hole of said fine holes, observing an X-ray emitted from the inside of said second fine hole due to the irradiation of said electron beam in order to carry out an element analysis of a residue substance existing at the opening bottom of said second fine hole and storing second analysis data resulting from said element analysis into said memory; and (3) reading out said first analysis data of said first fine hole and said second analysis data of said second fine hole from said memory, comparing said first analysis data with said second analysis data, forming a judgment as to whether or not a difference between said first analysis data and said second analysis data is smaller than a threshold value and using an outcome of said judgment to determine the opening states of said first and second fine holes, only said X-rays emitted from the insides of said first and second fine holes within the angular range $-\theta$ to $+\theta$ are observed where notation $\theta$ is an angle formed by said X-ray and the center axis of the irradiated electron beam and so defined that $\tan \theta$ is substantially equal to a/d whereas notations a and d are the radius and the depth of each of said first and second fine holes respectively.

2. A method for inspecting opening states of a plurality of fine holes with identical structures formed on the surface of a sample according to claim 1, wherein said electron beam is irradiated into said first and second fine holes by way of a condenser lens and an object lens and said X-rays emitted from the insides of said first and second fine holes are observed by using an X-ray detector having an energy discriminating capability installed in an internal space of said condenser lens, in an internal space of said object lens, between said condenser and object lenses or between said sample and said object lens.

3. A method for inspecting opening states of a plurality of fine holes with identical structures formed on the surface of a sample according to claim 1, wherein said sample is a semiconductor wafer in a process of manufacturing a semiconductor device and said fine holes are each a contact hole formed on the surface of said semiconductor wafer.

4. A method for inspecting opening states of a plurality of fine holes with identical structures formed on the surface of a sample according to claim 2, wherein said sample is a semiconductor wafer in a process of manufacturing a semiconductor device and said fine holes are each a contact hole formed on the surface of said semiconductor wafer.

5. A method for inspecting opening states of a plurality of fine holes with identical structures formed on the surface of a sample according to claim 1, wherein either of said first and second fine holes has been verified to have a good opening state in advance.

6. A method for inspecting opening states of a plurality of fine holes with identical structures formed on the surface of a sample, said method comprising the steps of:

irradiating a finely converged electron beam into a standard fine hole, one of said fine holes subjected to inspection using said method that has been verified to have a good opening state in advance, observing an X-ray emitted from the inside of said standard fine hole due to the irradiation of said electron beam in order to carry out an element analysis of a residue substance existing at the opening bottom of said standard fine hole and storing standard analysis data resulting from said element analysis into a memory;

irradiating a finely converged electron beam into a first fine hole of said fine holes, observing an X-ray emitted from the inside of said first fine hole due to the irradiation of said electron beam in order to carry out an element analysis of a residue substance existing at the opening bottom of said first fine hole and storing first analysis data resulting from said element analysis into said memory; and reading out said first analysis data of said first fine hole and said standard analysis data of said standard fine hole from said memory, comparing said first analysis data with said standard analysis data, forming a judgment as to whether or not a difference between said first analysis data and said standard analysis data is smaller than a threshold value and using an outcome of said judgment to determine the opening state of said first fine hole, only said X-rays emitted from the insides of said first and standard fine holes within the angular range $-\theta$ to $+\theta$ are observed, where notation $\theta$ is an angle formed by said X-ray and the center axis of the irradiated electron beam and so defined that $\tan \theta$ is substantially equal to a/d whereas notations a and d are the radius and the depth of each of said first and standard fine holes respectively.

7. A method for inspecting opening states of a plurality of fine holes with identical structures formed on the surface of a sample according to claim 6, wherein said electron beam is irradiated into said first and standard fine holes by way of a condenser lens and an object lens and said X-rays emitted from the insides of said first and standard fine holes are observed by using an X-ray detector having an energy discriminating capability installed in an internal space of said condenser lens, in an internal space of said object lens, between said condenser and object lenses or between said sample and said object lens.

8. A method for inspecting opening states of a plurality of fine holes with identical structures formed on the surface of a sample according to claim 6, wherein said sample is a semiconductor wafer in a process of manufacturing a semiconductor device and said fine holes are each a contact hole formed on the surface of said semiconductor wafer.

9. A method for inspecting opening states of a plurality of fine holes with identical structures formed on the surface of a sample, said method comprising the steps of:

(1) irradiating a finely converged electron beam into a first fine hole of said fine holes, observing an X-ray emitted from the inside of said first fine hole due to the irradiation of said electron beam in order to carry out an element analysis of a residue substance existing at the opening bottom of said first fine hole and storing first analysis data resulting from said element analysis into a memory:

(2) irradiating a finely converged electron beam into a second fine hole of said fine holes, observing an X-ray emitted from the inside of said second fine hole due to the irradiation of said electron beam in order to carry out an element analysis of a residue substance existing at the opening bottom of said second fine hole and storing second analysis data resulting from said element analysis into said memory; and (3) reading out said first analysis data of said first fine hole and said second analysis data of said second fine hole from said memory, comparing said first analysis data with said second analysis data, forming a judgment as to whether or not a difference between said first analysis data and said second analysis data is smaller than a threshold value and using an outcome of said judgment to determine the opening states of said first and second fine holes, only said X-rays emitted from the insides of said first and second fine holes within the angular range −20 degrees to +20 degrees from the center axis of the irradiated electron beam are observed.

10. A method for inspecting opening states of a plurality of fine holes with identical structures formed on the surface of a sample according to claim 9, wherein said electron beam is irradiated into said first and second fine holes by way of a condenser lens and an object lens and said X-rays emitted from the insides of said first and second fine holes are observed by using an X-ray detector having an energy discriminating capability installed in an internal space of said condenser lens, in an internal space of said object lens, between said condenser and object lenses or between said sample and said object lens.

11. A method for inspecting opening states of a plurality of fine holes with identical structures formed on the surface of a sample according to claim 9, wherein said sample is a semiconductor wafer in a process of manufacturing a semiconductor device and said fine holes are each a contact hole formed on the surface of said semiconductor wafer.

12. A method for inspecting opening states of a plurality of fine holes with identical structures formed on the surface of a sample according to claim 10, wherein said sample is a semiconductor wafer in a process of manufacturing a semiconductor device and said fine holes are each a contact hole formed on the surface of said semiconductor wafer.

13. A method for inspecting opening states of a plurality of fine holes with identical structures formed on the surface of a sample according to claim 9, wherein either of said first and second fine holes has been verified to have a good opening state in advance.

14. A method for inspecting opening states of a plurality of fine holes with identical structures formed on the surface of a sample, said method comprising the steps of:

irradiating a finely converged electron beam into a standard fine hole, one of said fine holes subjected to inspection using said method that has been verified to have a good opening state in advance, observing an X-ray emitted from the inside of said standard fine hole due to the irradiation of said electron beam in order to carry out an element analysis of a residue substance existing at the opening bottom of said standard fine hole and storing standard analysis data resulting from said element analysis into a memory;

irradiating a finely converged electron beam into a first fine hole of said fine holes, observing an X-ray emitted from the inside of said first fine hole due to the irradiation of said electron beam in order to carry out an element analysis of a residue substance existing at the opening bottom of said first fine hole and storing first analysis data resulting from said element analysis into said memory; and reading out said first analysis data of said first fine hole and said standard analysis data of said standard fine hole from said memory, comparing said first analysis data with said standard analysis data, forming a judgment as to whether or not a difference between said first analysis data and said standard analysis data is smaller than a threshold value and using an outcome of said judgment to determine the opening state of said first fine hole, only said X-rays emitted from said insides of said first and standard fine holes within the angular range −20 degrees to +20 degrees from the center axis of the irradiated electron beam are observed.

15. A method for inspecting opening states of a plurality of fine holes with identical structures formed on the surface of a sample according to claim 14, wherein said electron beam is irradiated into said first and standard fine holes by way of a condenser lens and an object lens and said X-rays emitted from said insides of said first and standard fine holes are observed by using an X-ray detector having an energy discriminating capability installed in an internal space of said condenser lens, in an internal space of said object lens, between said condenser and object lenses or between said sample and said object lens.

16. A method for inspecting opening states of a plurality of fine holes with identical structures formed on the surface of a sample according to claim 14, wherein said sample is a semiconductor wafer in a process of manufacturing a semiconductor device and said fine holes are each a contact hole formed on the surface of said semiconductor wafer.

17. An apparatus for inspecting opening states of a plurality of fine holes with identical structures formed on the surface of a sample, said apparatus comprising:

an electron-beam irradiating means for irradiating a finely converged electron beam into each of said fine holes;

an X-ray observing means for observing an X-ray emitted from the inside of said fine hole due to the irradiation of said electron beam;

an analysis means for carrying out an element analysis of a residue substance existing at the opening bottom of said fine hole on the basis of results of observing said X-ray;

a storage means for storing analysis data resulting from said element analysis; and a processing means for reading out pieces of analysis data of said fine holes from said storage means, comparing said pieces of analysis data with each other, only said X-rays emitted from the inside of said fine hole within the angular range $-\theta$ to $+\theta$ are observed where notation $\theta$ is an angle formed by said X-ray and the center axis of the irradiated electron beam and so defined that $\tan \theta$ is substantially equal to a/d whereas notations a and d are the radius and the depth of said fine hole respectively.

18. An apparatus for inspecting opening states of a plurality of fine holes with identical structures formed on the surface of a sample according to claim 17, wherein:

said electron-beam irradiating means comprises an object lens and a condenser lens for converging said electron beam irradiated into said fine holes;

said X-ray observing means has an X-ray detector having an energy discriminating capability; and said X-ray detector is installed in an internal space of said condenser lens, in an internal space of said object lens, between said condenser and object lenses or between the surface of said sample and said object lens.

19. An apparatus for inspecting opening states of a plurality of fine holes with identical structures formed on the surface of a sample, said apparatus comprising:

an electron-beam irradiating means for irradiating a finely converged electron beam into each of said fine holes;

an X-ray observing means for observing an X-ray emitted from the inside of said fine hole due to the irradiation of said electron beam;

an analysis means for carrying out an element analysis of a residue substance existing at the opening bottom of said fine hole on the basis of results of observing said X-ray;

a storage means for storing analysis data resulting from said element analysis; and a processing means for reading out pieces of analysis data of said fine holes from said storage means, comparing said pieces of analysis data with each other, only said X-rays emitted from the insides of said fine hole within the angular range −20 degrees to +20 degrees from the center axis of the irradiated electron beam are observed.

20. An apparatus for inspecting opening states of a plurality of fine holes with identical structures formed on the surface of a sample according to claim 19, wherein:

said electron-beam irradiating means comprises an object lens and a condenser lens for converging said electron beam irradiated into said fine holes:

said X-ray observing means has an X-ray detector having an energy discriminating capability; and said X-ray detector is installed in an internal space of said condenser lens, in an internal space of said object lens, between said condenser and object lenses or between the surface of said sample and said object lens.

* * * * *